(12) United States Patent
Wright et al.

(10) Patent No.: US 6,472,376 B2
(45) Date of Patent: *Oct. 29, 2002

(54) SUPPRESSION OF MALIGNANCY UTILIZING RIBONUCLEOTIDE REDUCTASE R1

(75) Inventors: Jim A. Wright; Aiping H. Young, both of Toronto (CA)

(73) Assignee: Genesense Technologies, Inc., Toronto (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/155,246

(22) PCT Filed: Mar. 18, 1998

(86) PCT No.: PCT/CA98/00242

§ 371 (c)(1),
(2), (4) Date: Dec. 17, 1998

(87) PCT Pub. No.: WO98/41231

PCT Pub. Date: Sep. 24, 1998

(65) Prior Publication Data

US 2002/0004488 A1 Jan. 10, 2002

Related U.S. Application Data

(60) Provisional application No. 60/060,669, filed on Oct. 2, 1997, and provisional application No. 60/040,837, filed on Mar. 19, 1997.

(51) Int. Cl.[7] .................. A61K 31/70; C12N 15/09; C12N 15/63; C12N 15/86
(52) U.S. Cl. .................. 514/44; 435/320.1; 435/455; 435/456
(58) Field of Search .................. 514/44; 536/23.1; 435/320.1, 325, 375, 455, 456; 424/93.21, 93.2, 93.1

(56) References Cited

U.S. PATENT DOCUMENTS 5,998,383 A 12/1999 Wright et al. .................. 514/44

FOREIGN PATENT DOCUMENTS

WO    WO 98 00532    1/1998

OTHER PUBLICATIONS

Ngo et al.; Computational Complexity, Protein Structure Prediction, and the Levinthal Paradox, 1994. In the Protein Folding Problem and Tertiary Structure Prediction, (Merz et al., eds), Birkhauser: Boston, pp. 491–494.*

Amara et al., 1995. "Altered regulation of message stability and tumor prometer–responsive cis–trans interactions of ribonucleotide reductase R1 and R2 messenger RNAs in hydroxyurea–resistant cells." Cancer Res. 55:4503–4506.

Bickel et al., 1993. "Pharmacologic effects in vivo in brain by vector–mediated peptide drug delivery" Proc. Natl. Acad. Sci. USA 90:2618–22.

Björklund et al., 1993. "Structure and promoter characterization of the gene encoding the large subunit (R1 protein) of mouse ribonucleotide reductase." Proc. Natl. Acad. Sci. USA 90:11322–11326.

Cares et al., 1985. "Cloned Mouse Ribonucleotide Reductase Subunit M1 cDNA Reveals Amino Acid Sequence Homology with *Escherichia coli* and Herpesvirus Ribonucleotide Reductases." J. Biol Chem. 260 (11):7015–22.

Chen et al., 1994. "Defining a novel ribonucleotide reductase R1 mRNA cis element that binds to an unique cytoplasmic transacting protein." Nucleic Acids Res., 22(22):4796–97.

Chen et al., 1993. "Mammalian ribonucleotide reductase R1 mRNA stability under normal and phorbol ester stimulating conditions: involvement of a cis–trans interaction at the 3'–untranslated region." EMBO J. 12(10):3977–3986.

Choy et al., 1988. "Molecular mechanisms of drug resistance involving ribonucleotide reductase: hydroxyurea resistance in a series of clonally related mouse cell lines selected in the presence of increasing drug concentrations." Cancer Res. 48: 2029–35.

Dang et al., 1999. "Gene Therapy and Translational Cancer Reseach." Clin. Cancer Res. 5:471–74.

Davis et al., 1994. "Purification, Characterization, and Localization of Subunit Interaction Area of Recombinant Mouse Ribonucleotide Reductase R1 Subunit." J. Biol. Chem. 269(37):23171–76.

Egan et al., 1987. "Transformation by oncogenes encoding protein kinases induces the metastic phenotype." Science 238:202–205.

Egan et al. 1987A. "Expression of H–ras Correlates with Metastatic Potential: Evidence for Direct Regulation of the Metastatic Phenotype in 10T1/2 and NIH 3T3 cells." Mol. Cell. Biol. 7(2):830–837.

(List continued on next page.)

*Primary Examiner*—Dave T. Nguyen
*Assistant Examiner*—Quang Nguyen
(74) *Attorney, Agent, or Firm*—Nath & Associates PLLC; Gary M. Nath; Todd L. Juneau

(57) ABSTRACT

The present invention provides a method of modulating the malignant properties of a cell in a human or other mammal by contacting a neoplastic cell with a growth modulating amount of an expressible nucleic acid sequence for ribonucleotide reductase R1 of the mammal. The present invention also provides and uses a growth modulating amount of the ribonucleotide reductase R1 protein or biologically active peptide to modulate the malignant properties of a cell in a human or other mammal. The method provides for a generally elevated expression of the R1 component of mammalian ribonucleotide reductase. The expressible nucleic acid sequence can be in the form of a vector for gene therapy.

10 Claims, 3 Drawing Sheets

OTHER PUBLICATIONS

Fan, H. et al. 1996. "Suppression of Malignancy by the 3'Untranslated Regions of Ribonucleotide Reductase R1 and R2 Messenger RNAs." Cancer Res. 56:4366–69.

Fan, H. et al. 1997. "The R1 component of mamalian ribonucleotide reductase has malignacy–suppressing activity as demonstrated by gene transfer experiments." Proc. Natl. Acad. Sci. USA. 94:13181–13186.

Gilboa et al., 1986. "Transfer and Expression of Cloned Genes Using Retroviral Vectors." Biotechniques 4(6): 504–512.

Hanania et al., 1995. "Recent advances in the application of gene therapy to human disease." Am. J. Med. 99:537–552.

Hurta et al., 1994. "Alterations in the Cyclic AMP Signal transduction pathway regulating ribonucleotide reductase gene expression in malignant H–ras transformed cell lines." J. Cell. Physiology 158:187–97.

Mader, R.M et al., 1996. "A deletion of 1851 nucleotides in the ribonucleotide reductase mRNA is associated with colorectal cancer." Proceedings of the American Association of Cancer Research 37:3745.

Mann et al., 1988. "Ribonucleotide reductase M1 Subunit in Cellular Proliferation, Quiescence and Differentiation" Cancer Res. 48:5151–56.

McClarty et al., 1990. "Increased Ferritin Gene Expression is Associated with Increased Ribonucleotide Reductase Gene Expression and the Establishment of Hydroxyurea Resistance in mammalian Cells." J. Biol. Chem. 265(13): 7539–47.

McCluskie, M.J. et al., 1999. "Route and Method of Delivery of DNA Vaccine Influence Immune Responses in Mice and Non–human Primates." Mol. Med. 5:287–300.

Miller et al., 1993. "Use of Retroviral Vectors for Gene Transfer and Expression." Meth. Enzymol. 217. 581–599.

Pakula, A.A. et al., 1989. "Genetic Analysis of Protein Stability and Function." Annu. Rev. Genet. 23:289–310.

Pavloff, N. et al., 1992. "Seqence analysis of the large and small subunits of human ribonucleotide reductase." DNA Seq. 2:227–234.

Reichard, 1993. "From RNA to DNA, Why so many Ribonucleotide Reductases?" Science 60:1773–77.

Saeki, et al., 1995. "Immunohistochemical detection of ribonucleotide reductase in human breast tumors." Int. J. Oncol. 6:523–29.

Thelander et al., 1980. "Ribonucleotide Reductase from Calf Thymus. Separation of the enzyme into two nonidentical subunits, proteins M1 and M2." J. Biol. Chem. 255(15): 7426–32.

Toloza, E.M. et al., 1996. "In vivo cancer gene therapy with a recombinant interleukin–2 adenovirus vector." Cancer Gene Therapy. 30(1) :11–17.

Tonin et al., 1987. "Chromosomal assignment of amplified genes in hydroxyurea resistant hamster cells." Cytogenet. Cell. Genet 45:102–108.

Wivel, N.A. et al., 1998. "Methods of Gene Delivery" Hematol. Oncol. Clin. North Am. 12(3) :483–501.

Wright et al., 1989. "Hydrocyurea and related compounds" *Drug Resistance in Mammalian Cells*, R.S. Gupta Ed. (CRC Press, Boca Raton, FL, 1989) Chapter 2, vol. 1:15–27.

Björklund et al., "S–Phase–Specific Expression of Mammalian Ribonucleotide Reductase R1 and R2 Subunit mRNAs", *Biochemistry*, 29, pp. 5452–5458 (1990).

Blaese, "Gene Therapy for Cancer", *Scientific American*, 276(6), pp. 111–115 (1997).

Chen et al., "Regulation of mammalian ribonucleotide reductase R1 mRNA stability is mediated by a ribonulceotide reductase R1 mRNA 3'–untranslated region cis–trans interaction through a protein kinase C–controlled pathway", *Biochem. J.*, 302, pp. 125–132 (1994).

Deonarain, "Ligand–targeted receptor–mediated vectors for gene delivery", *Exp. Opin. Ther. Patents*, 8(1), pp. 53–69 (1998).

Filatov et al., "Induction of the Mouse Ribonucleotide Reductase R1 and R2 Genes in Response to DNA Damage by UV Light", *J. Biol. Chem.*, 271, pp. 23698–23704 (1996).

Hurta et al., "Alteration in the Activity and Regulation of Mammalian Ribonucleotide Reductase By Chlorambucil, a DNA Damaging Agent", *J. Biol. Chem.*, 267, pp. 7066–7071 (1992).

Hurta et al., "Early Induction of Ribonucleotide Reductase Gene Expression by Transforming Growth Factor $\beta_1$", *J. Cell. Biochem.*, 57, pp. 543–556 (1995).

Jensen et al., "Identification of genes expressed in premalignant breast disease by microscopy–directed cloning", *Proc. Natl. Acad. Sci. USA*, 91, pp. 9257–9261 (1994).

Hurta et al., "Malignant Transformation by H–ras Results in Aberrant Regulation of Ribonucleotide Reductase Gene Expression by Transforming Growth Factor–$\beta_1$", *J. Cell. Biochem.*, 57, pp. 543–556 (1995).

Miller et al., "Targeted vectors for gene therapy", *FASEB J.*, 9, pp. 190–199 (1995).

Parsons, J.A., *Peptide Hormones*, University Park Press: Baltimore, Chapter 14, pp. 491–495 (1976).

Parker et al., "Human M1 subunit of ribonucleotide reductase: cDNA sequence and expression in stimulated lymphocytes", *Nucl. Acids Res.*, 19(13), p. 3741 (1991).

Rudinger, *Peptide Hormones*, University Park Press: Baltimore, Chapter 1, pp. 1–7 (1976).

Thelander et al., "Isolation and Characterization of Expressible cDNA Clones Encoding the M1 and M2 Subunits of Mouse Ribonucleotide Reductase", *Mol. Cell. Biol.*, 6(10), pp. 3433–3442 (1986).

Thelander et al., "Ribonucleotide Reductase from Calf Thymus", *J. Biol. Chem.*, 255(15), pp. 7426–7432 (1980).

Verma et al., "Gene therapy–promises, problems and prospects", *Nature*, 389, pp. 239–242 (1997).

Weber, "Biochemical Strategy of Cancer Cells and the Design of Chemotherapy", *Cancer Res.*, 43, pp. 3466–3492 (1983).

Wright, "Altered Mammalian Ribonucleoside Diphosphate Reductase From Mutant Cell Lines", *Intl. Encycl. Pharmacol. Therapeut.*, 128, pp. 89–111 (1989).

Wright et al., "Regulation and drug resistance mechanisms of mammalian ribonucleotide reductase, and the significance to DNA synthesis", *Biochem. Cell. Biol.*, 68, pp. 1364–1371 (1990).

Wright et al., "Antisense molecules and their potential for the treatment of cancer and AIDS", *Cancer J.*, 8(4), pp. 185–189 (1995).

Wright et al., "Genetic Regulation of Metastatic Progression", *Anticancer Res.*, 10, pp. 1247–1256 (1990).

* cited by examiner

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 3083 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
GGGGATTTGG ATTGTTGCGC CTCTGCTCTG AAGAAAGTGC TGTCTGGCTG GAACTCCAGT      60

TCTTTCCCCT GAGCAGCGCC TGGAACCTAA CCCTTCCCAC TCTGTCACCT TCTCGATCCC     120

GCCGGCGCTT TAGAGCCGCA GTCCAGTCTT GGATCCTTCA GAGCCTCAGC CACTAGCTGC     180

GATGCATGTG ATCAAGCGAG ATGGCCGCCA AGAACGAGTC ATGTTTGACA AAATTACATC     240

TCGAATCCAG AAGCTTTGTT ATGGACTCAA TATGGATTTT GTTGATCCTG CTCAGATCAC     300

CATGAAAGTA ATCCAAGGCT TGTACAGTGG GGTCACCACA GTGGAACTAG ATACTTTGGC     360

TGCTGAAACA GCTGCAACCT TGACTACTAA GCACCCTGAC TATGCTATCC TGGCAGCCAG     420
```

-continued

```
GATCGCTGTC TCTAACTTGC ACAAAGAAAC AAAGAAAGTG TTCAGTGATG TGATGGAAGA       480

CCTCTATAAC TACATAAATC CACATAATGG CAAACACTCT CCCATGGTGG CCAAGTCAAC       540

ATTGGATATT GTTCTGGCCA ATAAAGATCG CCTGAATTCT GCTATTATCT ATGACCGAGA       600

TTTCTCTTAC AATTACTTCG GCTTTAAGAC GCTAGAGCGG TCTTATTTGT TGAAGATCAA       660

TGGAAAAGTG GCTGAAAGAC CACAACATAT GTTGATGAGA GTATCTGTTG GGATCCACAA       720

AGAAGACATT GATGCAGCAA TTGAAACATA TAATCTTCTT TCTGAGAGGT GGTTTACTCA       780

TGCTTCGCCC ACTCTCTTCA ATGCTGGTAC CAACCGCCCG CAACTTTCTA GCTGTTTTCT       840

TCTGAGTATG AAAGATGACA GCATTGAAGG CATTTATGAC ACTCTAAAGC AATGTGCATT       900

GATTTCTAAG TCTGCTGGAG GAATTGGTGT TGCTGTGAGT TGTATTCGGG CTACTGGCAG       960

CTACATTGCT GGGACTAATG GCAATTCCAA TGGCCTTGTA CCGATGCTGA GAGTATATAA      1020

CAACACAGCT CGATATGTGG ATCAAGGTGG GAACAAGCGT CCTGGGGCAT TTGCTATTTA      1080

CCTGGAGCCT TGGCATTTAG ACATCTTTGA ATTCCTTGAT TTAAAGAAGA ACACAGGAAA      1140

GGAAGAGCAG CGTGCCAGAG ATCTTTTCTT TGCTCTTTGG ATTCCGGATC TCTTCATGAA      1200

ACGAGTGGAG ACTAATCAGG ACTGGTCTTT GATGTGTCCA AATGAGTGTC CTGGTCTGGA      1260

TGAGGTTTGG GGAGAGGAAT TGAGAAACT ATATGCAAGT TATGAGAAAC AAGGTCGTGT       1320

CCGCAAAGTT GTAAAAGCTC AGCAGCTTTG GTATGCCATC ATTGAGTCTC AGACGGAAAC      1380

AGGCACCCCG TATATGCTCT ACAAAGATTC CTGTAATCGA AAGAGCAACC AGCAGAACCT      1440

GGGAACCATC AAATGCAGCA ACCTGTGCAC AGAAATAGTG GAGTACACCA GCAAAGATGA      1500

GGTTGCTGTT TGTAATTTGG CTTCCCTGGC CCTGAATATG TATGTCACAT CAGAACACAC      1560

ATACGACTTT AAGAAGTTGG CTGAAGTCAC TAAAGTCGTT GTCCGAAACT TGAATAAAAT      1620

TATTGATATA AACTACTATC CTGTACCAGA GGCATGCCTA TCAAATAAAC GCCATCGCCC      1680

CATTGGAATT GGGGTACAAG GTCTGGCAGA TGCTTTTATC CTGATGAGAT ACCCTTTTGA      1740

GAGTGCAGAA GCCCAGTTAC TGAATAAGCA GATCTTTGAA ACTATTTATT ATGGTGCTCT      1800

GGAAGCCAGC TGTGACCTTG CCAAGGAGCA GGGCCCATAC GAAACCTATG AGGGCTCTCC      1860

AGTTAGCAAA GGAATTCTTC AGTATGATAT GTGGAATGTT ACTCCTACAG ACCTATGGGA      1920

CTGGAAGGTT CTCAAGGAGA AGATTGCAAA GTATGGTATA AGAAACAGTT TACTTATTGC      1980

CCCGATGCCT ACAGCTTCCA CTGCTCAGAT CCTGGGGAAT AATGAGTCCA TTGAACCTTA      2040

CACCAGCAAC ATCTATACTC GCAGAGTCTT GTCAGGAGAA TTTCAGATTG TAAATCCTCA      2100

CTTATTGAAA GATCTTACCG AGCGGGGCCT ATGGCATGAA GAGATGAAAA ACCAGATTAT      2160

TGCATGCAAT GGCTCTATTC AGAGCATACC AGAAATTCCT GATGACCTGA GCAACTTTA      2220

TAAAACTGTG TGGGAAATCT CTCAGAAAAC TGTTCTCAAG ATGGCAGCTG AGAGAGGTGC      2280

TTTCATTGAT CAAAGCCAAT CTTTGAACAT CCACATTGCT GAGCCTAACT ATGGCAAACT      2340

CACTAGTATG CACTTCTACG GCTGGAAGCA GGGTTTGAAG ACTGGGATGT ATTATTTAAG      2400

GACAAGACCA GCAGCTAATC CAATCCAGTT CACTCTAAAT AAGGAGAAGC TAAAAGATAA      2460

AGAAAAGGTA TCAAAGAGG AAGAAGAGAA GGAGAGGAAC ACAGCAGCCA TGGTGTGCTC       2520

TTTGGAGAAT AGAGATGAAT GTCTGATGTG TGGATCCTGA GGAAAGACTT GGAAGAGACC      2580

AGCATGTCTT CAGTAGCCAA ACTACTTCTT GAGCATAGAT AGGTATAGTG GGTTTGCTTG      2640

AGGTGGTAAG GCTTTGCTGG ACCCTGTTGC AGGCAAAAGG AGTAATTGAT TTAAAGTACT      2700

GTTAATGATG TTAATGATTT TTTTTTAAAC TCATATATTG GGATTTTCAC CAAAATAATG      2760

CTTTTGAAAA AAAGAAAAAA AAAACGGATA TATTGAGAAT CAAAGTAGAA GTTTTAGGAA      2820
```

```
TGCAAAATAA GTCATCTTGC ATACAGGGAG TGGTTAAGTA AGGTTTCATC ACCCATTTAG    2880

CATGCTTTTC TGAAGACTTC AGTTTTGTTA AGGAGATTTA GTTTTACTGC TTTGACTGGT    2940

GGGTCTCTAG AAGCAAAACT GAGTGATAAC TCATGAGAAG TACTGATAGG ACCTTTATCT    3000

GGATATGGTC CTATAGGTTA TTCTGAAATA AAGATAAACA TTTCTAAGTG AAAAAAAAAA    3060

AAAAAAAAAA AAAAAAAAA AAA                                            3083
```

(2) INFORMATION FOR SEQ ID NO:2:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: NO (xi) SEQUENCE DESCRIPTION: SEQ ID NO:2:

```
ACCGCTCGAG CCACCATGGA ACAAAAGCTT ATTTCTGAAG AAGACTTGAT GCATGTGATC     60

AAGCGAGA                                                              68
```

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (xi) SEQUENCE DESCRIPTION: SEQ ID NO:3:

```
CCGCTCGAAT CAGGATCCAC ACATCAG                                         27
```

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (xi) SEQUENCE DESCRIPTION: SEQ ID NO:4:

```
GCCTCGAGCT GACAGTCGTC TCTGTCCCT                                       29
```

(2) INFORMATION FOR SEQ ID NO:5:

(i) SEQUENCE CHARACTERISTICS:
        (A) LENGTH: 35 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (xi) SEQUENCE DESCRIPTION: SEQ ID NO:5:

TAAAGCTTAT CACTTAGAAA TGTTTATTTC AAAAT                                              35
```

SUPPRESSION OF MALIGNANCY UTILIZING RIBONUCLEOTIDE REDUCTASE R1

RELATED APPLICATIONS

The present application is a 371 of PCT/CA98/00242 filed Mar. 18, 1998, which claims priority of U.S. Provisional Patent Application Ser. No. 60/040,837, filed Mar. 19, 1997, and U.S. Ser. No. 60/060,669, filed Oct. 2, 1997, each incorporated herein by reference in their entirety.

BACKGROUND OF THE INVENTION

1. Field of the Invention

The field of this invention relates to methods of controlling the tumorigenicity and/or metastasis of neoplastic cells. Specifically it relates to the use of the R1 gene sequence of ribonucleotide reductase and gene product thereof to suppress malignancy.

2. Description of Related Art

The first unique step leading to DNA synthesis is the conversion of ribonucleotides to their corresponding deoxyribonucleotides, a reaction that is catalyzed in a cell cycle specific manner by the housekeeping gene ribonucleotide reductase [Lewis et al., 1978; Reichard, 1993; Wright, 1989a; Wright et al., 1990a; Stubbe, 1989]. The mammalian enzyme is composed of two dissimilar dimeric protein components often called R1 and R2, which are encoded by two different genes located on different chromosomes [Björklund et al., 1993; Tonin et al., 1987]. Mammalian protein R1 is a homodimeric structure and has substrate sites and allosteric effector sites that control enzyme activity and substrate specificity [Wright, 1989b; Thelander et al., 1980; Caras et al., 1985; Wright et al., 1990a]. Protein R2 is a homodimer and forms two equivalent dinuclear iron centers that stabilizes a tyrosyl free radical required for catalysis [Wright et al., 1990a; Thelander et al., 1985; McClarty et al., 1990]. R1 and R2 proteins interact at their C-terminal ends to form an active holoenzyme [Reichard, 1993; Wright et al., 1990a; Davis et al., 1994]. Ribonucleotide reductase serves other biological functions in addition to providing substrates for DNA replication. For example, its activity can be induced outside the S phase by DNA cross-linking agents such as chlorambucil and UV irradiation, indicating a role for the enzyme in the DNA repair process [Hurta and Wright, 1992].

R1 and R2 are differentially regulated during the cell cycle. There is an S-phase correlated increase in the R2 protein resulting from its de novo synthesis [Lewis et al., 1978; Mann et al, 1988]. The activity of ribonucleotide reductase, and therefore DNA synthesis and cell proliferation, is controlled in proliferating cells during the cell cycle by the synthesis and degradation of the R2 component [Eriksson et al., 1984; Choy et al, 1988]. The rate-limiting R2 component is a phosphoprotein capable of being phosphorylated by the CDC2 and CDK2 protein kinase mediators of cell cycle progression [Chan et al., 1993], and contains non-heme iron that stabilizes an unique tyrosyl free radical required for enzyme activity [Reichard, 1993; McClarty et al., 1990].

The levels of the R1 protein do not appear to change substantially during the cell cycle of proliferating cells and can be detected throughout the cell cycle. Synthesis of R1 mRNA, like R2 mRNA appears to occur mainly during S phase [Eriksson et al., 1984; Choy et al., 1988; Mann et al., 1988]. The broader distribution of the R1 protein during the cell cycle is attributed to its longer half life as compared to the R2 protein [Choy et al., 1988; Mann et al., 1988].

Regulation of ribonucleotide reductase, and particularly the R2 component, is markedly altered in malignant cells exposed to tumor promoters or to the growth factor TGF-β [Amara, et al., 1994; Chen et al., 1993; Amara et al., 1995b; Hurta and Wright, 1995; Hurta et al., 1991]. An R1 deletion can be detected in some human colorectal carcinomas [Glenney, 1986]. Higher levels of enzyme activity have been observed in cultured malignant cells when compared to nonmalignant cells [Weber, 1983; Takeda and Weber, 1981; Wright et al., 1989a], and increased levels of R2 protein and R2 mRNA have been found in pre-malignant and malignant tissues as compared to normal control tissue samples [Saeki et al., 1995; Jensen et al., 1994]. Regulation of ribonucleotide reductase, and in particular the R2 component, is significantly elevated in transformed cells exposed to tumor promoters, or to transforming growth factor β in growth factor mediated mechanisms of tumor progression [Amara et al., 1996; Chen et al., 1993; Amara et al, 1995b].

Currently chemotherapeutic compounds like hydroxyurea inhibit ribonucleotide reductase activity by destabilizing the iron center of the R2 protein causing the destruction of the tyrosyl free radical [McClarty et al., 1990], and preventing cells from progressing through S-phase of the cell cycle [Ashihara and Baserga, 1979]. Such drugs have a limited usefulness in treatment of human cancer and therefore additional approaches which target ribonucleotide reductase are needed.

Breakthroughs in molecular biology and the human genome project have opened previously unforeseen possibilities for targeted intervention with mammalian gene expression [Blaese, 1997; Felgner, 1997]. These include approaches such as gene therapy to introduce into neoplastic cells genetic control sequences and specific proteins to kill proliferating cells. It would be useful to utilize this approach to modify expression of ribonucleotide reductase in cells in which growth must be controlled such as a neoplastic cells.

SUMMARY OF THE INVENTION

According to the present invention, a use of a growth modulating amount of an expressible nucleic acid sequence for ribonucleotide reductase R1 to modulate the tumorigenic and metastatic properties of a cell in a human or other mammal is disclosed. The present invention also provides a method of modulating the tumorigenic and metastatic properties of a cell in a human or other mammal. The method includes the steps of contacting a neoplastic cell with a growth modulating amount of an expressible nucleic acid sequence for ribonucleotide reductase R1 of the mammal and in an embodiment for humans can be SEQ ID No:1 or the specific R1 coding sequence thereof. The expressible nucleic acid sequence can be delivered via a gene delivery vehicle which can be in the form of a vector for gene therapy. Alternatively in an embodiment the R1 gene product protein or biologically active peptide thereof which can be in the form of a pharmaceutical composition can be delivered to the cell to be controlled. The method and use and composition of the present invention provides for a generally elevated expression of the R1 component of mammalian ribonucleotide reductase in a cell to be controlled.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
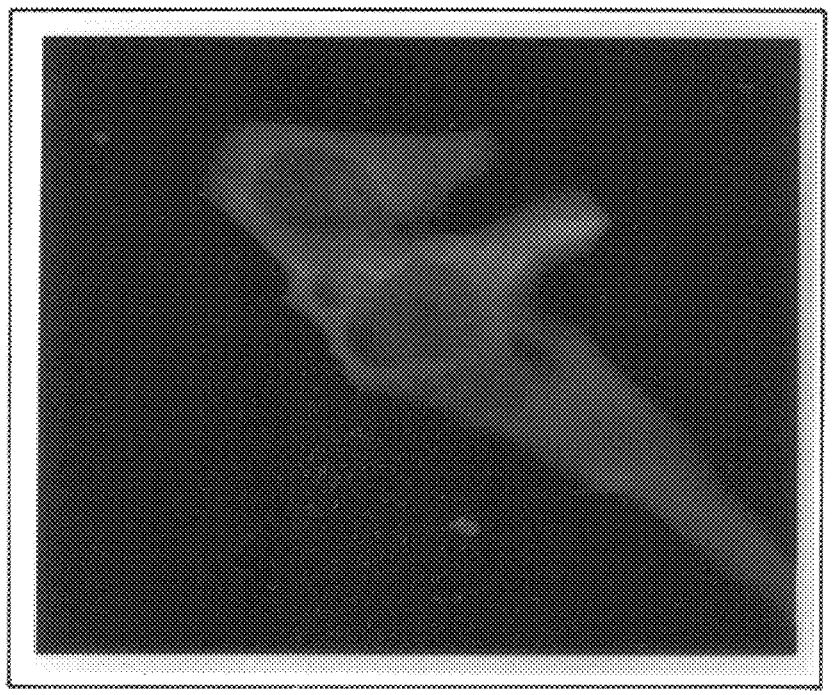
FIG. 1A–B are photographs showing an analysis of Myc-epitope-tagged R1 expression [Fan et al, 1996b] from pSHD/mR1 transiently transfected BHK cells by the indirect immunofluorescence assay (A), and from the stable retroviral packaging cell line PA/mR1 by radioimmunoprecipitation (B). Anti-Myc epitope antibody 9E10 was used for both assays.

The present invention provides a method of modulating, including tumor suppression, the malignant properties of a cell in a human or other mammal by increasing expression of ribonucleotide reductase R1 in the cell by using pharmacologic means or gene therapy means. For example, a neoplastic cell can be contacted with a growth modulating amount of an expressible nucleic acid sequence of ribonucleotide reductase R1 (for humans see SEQ ID No:1) of the mammal providing a generally elevated expression of the R1 component of mammalian ribonucleotide reductase. In an alternative embodiment the cell is treated pharmacologically to increase R1 expression. In a further embodiment, the cell is contacted with the ribonucleotide reductase R1 protein or biologically active analogues or derivatives thereof. The expressible nucleic acid sequence is generally provided in a gene delivery vehicle which can be in the form of a vector for gene therapy.

The present invention further provides and uses a pharmaceutical composition for modulating malignant cell growth in a human or other mammal consisting of an effective amount of an expressible nucleic acid sequence for ribonucleotide reductase R1 of the mammal or analogues thereof, and which may be in the form of a vector and a pharmaceutically physiologically acceptable carrier or diluent. In an embodiment the present invention further provides and uses a pharmaceutical composition for modulating malignant cell growth in a human or other mammal consisting of an effective amount of ribonucleotide reductase R1 protein or biologically active analogues or derivatives thereof of the mammal and a pharmaceutically physiologically acceptable carrier or diluent.

The cell can be treated pharmacologically to increase R1 expression as is known in the art as for example drugs that increase expression by activating appropriate pathways or which increase mRNA stability. For example, stimulating cAMP synthesis increases R1 expression in cells in which there is a functional gene using either forskolin or cholera toxin [Hurta and Wright, 1994]. Another agent which can be used includes 3-isobutyl-1-methylxanthene (an inhibitor of cAMP degradation). The expression of R1 mRNA is regulated by a protein kinase C pathway, therefore drugs which increase message stability in this pathway would increase the availability of R1 mRNA [Chen et al, 1994A].

By modulating is meant suppression of cellular transformation characteristics such as anchorage independent growth and other characteristics known in the art and as exemplified herein in the Examples. Modulating encompasses tumor suppressive activity and activity which slows tumor growth and/or causes tumor regression and reduction of tumorigenicity and metastatic potential. Modulating can include inhibition of any abnormal cell or tissue growth or proliferation and can include returning a cell to a normal phenotype.

The growth modulating amount of an expressible nucleic acid sequence of ribonucleotide reductase, which may be in the form of a gene therapy vector, or the R1 gene product itself or analogues or derivatives thereof, or drugs to increase R1 cellular expression of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to tumor shrinkage and to improved survival rate or more rapid recovery, or improvement or elimination of symptoms and other indicators as are selected as appropriate measures by those skilled in the art.

By gene therapy as used herein refers to the transfer of genetic material (e.g DNA or RNA) of interest into a host to treat or prevent a genetic or acquired disease or condition phenotype. The genetic material of interest encodes a product (e.g. a protein, polypeptide, peptide or functional RNA) whose production in vivo is desired. For example, the genetic material of interest can encode a hormone, receptor, enzyme, polypeptide or peptide of therapeutic value. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to produce the transfected gene product in situ.

In in vivo gene therapy, target cells are not removed from the subject rather the gene to be transferred is introduced into the cells of the recipient organism in situ, that is within the recipient. Alternatively, if the host gene is defective, the gene is repaired in situ [Culver, 1998]. These genetically altered cells have been shown to produce the transfected gene product in situ.

The gene expression vehicle is capable of delivery/transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore as used herein the expression vehicle may, as needed, not include the 5'UTR and/or 3'UTR shown in SEQ ID No:1 and only include the specific amino acid coding region for R1, an R1 peptide or this coding region may be modified to produce an R1 analog.

The expression vehicle can include a promotor for controlling transcription of the heterologous material and can be either a constitutive or inducible promotor to allow selective transcription. Enhancers that may be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene as described herein below.

Vectors are one means of a gene delivery vehicle and can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods as well see U.S. Pat. Nos. 5,698,443; 5,686,278; 5,538,885; 5,691,176; 5,585,254; 5,614,396; 5,670,488; 5,599,712; 5,645,829; 5,641,680 and 5,688,773.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor, which includes most cancers of epithelial origin as well as others. This vector as well as others that exhibit similar desired functions can be used to treat a mixed population of cells and can include, for example, an in vitro or ex vivo culture of cells, a tissue or a human subject (see for example U.S. Pat. Nos. 5,691,176; 5,585,254; 5,670,488; 5,681,731)

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of an antibiotic.

In addition, recombinant viral vectors are useful for in vivo expression of a desired nucleic acid because they offer advantages such as lateral infection and targeting specificity. Lateral infection is inherent in the life cycle of, for example, retroviruses and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement needed with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

By Analogue as used herein is meant a variant (alternatively the terms alteration, amino acid sequence alteration, amino acid sequence variant can be used) with some differences in their amino acid sequences as compared to the native amino acid sequence of ribonucleotide reductase R1. Ordinarily, the analogue will be generally at least 70% homologous over any portion that is functionally relevant. In more preferred embodiments the homology will be at least 80% and can approach 95% homology to the amino acid sequence. The amino acid or nucleotide sequence of an analog may differ from that of the ribonucleotide reductase R1 protein when at least one residue is deleted, inserted or substituted, but the protein remains functional, that is biologically active. Differences in glycosylation can provide analogues.

By derivative as used herein can mean a peptide fragment of the ribonucleotide reductase R1 protein that provides the same or similar biological activity as shown herein in the Examples. It is understood that the peptide fragment may not be as effective as the full protein molecule but that it can still provide biological activity as measured herein in the Examples. The peptide fragment may however provide better pharmokinetic parameters than the entire protein for various delivery systems and therefore provide an alternative. The specific amino acid coding region for R1 may be modified to produce a biologically active R1 peptide derivative for use in gene therapy as described herein above. Derivatives can further refer to pharmaceutically acceptable modifications of the protein or peptide as is known in the art to improve fluidity and solubility without significantly changing biological activity.

Biologically active refers to the biological property of the molecule, analogue or derivative, and in this context means an in vivo effector or activity that is directly or indirectly performed by a naturally occurring (native) ribonucleotide reductase R1, particularly as measured and defined in the Examples. Effector functions include but are not limited to include receptor binding, any enzymatic activity or enzyme modulatory activity, any carrier binding activity, any hormonal activity, any activity in promoting or inhibiting adhesion of cells to extracellular matrix or cell surface molecules, or any structural role. The biological activity of the analogues or derivatives can be determined as disclosed in the Examples as is known to those skilled in the art.

The ribonucleotide reductase R1 protein or biologically active analogues or derivatives thereof can be prepared by synthesizing the protein or peptide based on the sequence, or prepared recombinantly by cloning techniques or the natural gene product and/or portions thereof may be isolated and used as is known in the art.

In administering the ribonucleotide reductase R1 and its biologically active analogues or derivatives, doses may be single doses or multiple doses over a period of several days to several months or until diminution of the disease is achieved. The treatment generally has a length proportional to the length of the disease process and drug effectiveness and the patient species being treated. Optimal dosing schedules may be calculated using measurements of drug accumulation in the body. Practitioners of ordinary skill in the art can readily determine optimum dosages, dosing methodologies, and repetition rates. Optimum dosages may vary depending on the relative potency of ribonucleotide reductase R1, biologically active analogues and derivatives, and can generally be determined based on $ED_{50}$ values in in vitro and in vivo animal studies and clinical trials.

The ribonucleotide reductase R1 and its biologically active analogues or derivatives may be the active ingredient in combination with pharmaceutically acceptable carriers, diluents, adjuvants and vehicles in a pharmaceutical composition. The composition can be administered orally, subcutaneously, topically, or parenterally including intravenous, intraarterial, intramuscular, intraperitoneally, and intranasal administration as well as intrathecal and infusion techniques. Suppositories and implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

When administering parenterally, the pharmaceutical composition of the present invention will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

Topical administration can be effected by any method known in the art and can include incorporation of the pharmaceutical composition into creams, ointments or transdermal patches.

A pharmacological formulation can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. No. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation utilized in the present invention can be administered orally to the patient. Conventional methods such as administering the compounds in tablets, suspensions, solutions, emulsions, capsules, powders, syrups and the like are usable.

Known techniques which deliver orally, subcutaneously or parenterally including intravenous, intraarterial, intramuscular, intraperitoneally, and intranasal administration as well as intrathecal and infusion techniques and retain the biological activity are preferred.

For delivery within the CNS intrathecal delivery can be used with for example an Ommaya reservoir. U.S. Pat. No. 5,455,044 provides for use of a dispersion system for CNS delivery or see U.S. Pat. No. 5,558,852 for a discussion of CNS delivery. In addition, pharmacological formulations that cross the blood-brain barrier can be administered. [Betz et al., 1994; Brem et a;., 1993] Such formulations can take advantage of methods now available to produce chimeric peptides in which the present invention is coupled to a brain transport vector allowing transportation across the barrier [Pardridge, et al., 1992; Pardridge, 1992; Bickel, et al., 1993]. Further, in appropriate cases blood-brain barrier disruption can be utilized [Neuwelt et al., 1980].

The results obtained in the Examples herein below demonstrate for the first time, that elevated expression of the R1 component of mammalian ribonucleotide reductase can suppress cellular transformation characteristics such as anchorage independent growth. Consistent with these results was the observation that expression of the R1 sequence in the antisense orientation led to a decrease in R1 protein and an increase in cellular transformation, as indicated by a marked elevation in anchorage independent growth ability. Similar to the mouse cell lines used in this study, overexpression of R1 in the human tumor Colo 320HSR cell line also resulted in decreased anchorage independent growth, indicating that R1 can exert a suppressing function in human cells too. Clearly, the levels of R1 gene expression are important in determining malignant potential and a decreased expression can increase malignancy related characteristics.

Expression of R1 was also capable of suppressing tumorigenicity and malignant potential in vivo as shown in the Examples. Three of the four cell lines tested exhibited increased tumor latency and decreased tumor growth properties in animals in the presence of increased R1 expression.

Interestingly, R2 overexpression has been shown previously to have an opposite effect on transformation, tumorigenic and malignant properties of cells. Overexpression of R2 cooperates with activated oncogenes to promote tumor progression, and this process appears to be mediated at least partly through changes in the MAPK pathway [Fan, et al., 1996a]. Previous work [Fan, et al., 1996a], and the present study demonstrate that the two different proteins, R1 and R2 which are required for ribonucleotide reduction, a key rate-limiting activity in DNA synthesis [Reichard, 1993; Wright, 1989a], have opposing and very dramatic malignancy-relevant effects when overexpressed in tumor cells. It can be suggested that there is a delicate balance between R1 and R2 levels in cells, and that abrogation of this balance significantly modifies the malignant potential of tumor cells. As shown in the Examples herein below changing the regulatory expression of R1 expression can act as a novel malignancy suppressor.

The above discussion provides a factual basis for the use of R1 as a malignancy suppressor. The methods used with and the utility of the present invention can be shown by the following non-limiting examples and accompanying figures.

EXAMPLES

General Methods

GENERAL METHODS IN MOLECULAR BIOLOGY: Standard molecular biology techniques known in the art and not specifically described were generally followed as in Sambrook et al., *Molecular Cloning: A Laboratory Manual*, Cold Springs Harbor Laboratory, New York (1989, 1992); in Ausubel et al., Current Protocols in Molecular Biology, John Wiley and Sons, Baltimore, Md. (1989); and in Perbal, *A Practical Guide to Molecular Cloning*, John Wiley & Sons, New York (1988). Polymerase chain reaction (PCR) was carried out generally as in PCR Protocols: *A Guide To Methods And Applications*, Academic Press, San Diego, Calif. (1990).

VECTORS: Vectors can be constructed for the present invention by those skilled in the art and should contain all expression elements necessary to achieve the desired transcription of the sequences. The expression elements can be selected to allow expression only in the cell being targeted. Other beneficial characteristics can also be contained within the vectors such as mechanisms for recovery of the nucleic acids in a different form. One of ordinary skill in the art will know which expression elements are compatible with a particular cell type. The vectors can be introduced into cells or tissues by any one of a variety of known methods within the art as described herein.

Expression Vectors. The human Myc epitope-tagged mouse R1 cDNA [Fan et al, 1996b] was obtained by polymerase chain reaction (PCR) using the 5'-primer ACCGCTCGAGCCACC<u>ATGGAACAAAAGCTTATTT-CTGAAGAAGACTTG</u>ATGCATGTGATCAAGCGAGA (SEQ ID No:2; where the Kozak sequence, a possible ribosomal binding signal [Kozak, 1987], is in italics; the sequence encoding the human Myc epitope is underlined; and the natural ATG initiation codon is in bold), and the 3'-primer CCGCTCGAATCAGGATCCACACATCAG (SEQ ID No:3; where the termination codon is in bold), and the template plasmid pcD-M1 [Thelander and Berg, 1986]. The PCR product was treated with proteinase K, digested with Xho1, gel purified and ligated to dephosphorylated Xho1. -digested pLXSHD plasmid [Miller, et al., 1993; Fan, et al., 1996c], to generate the retroviral vector pSHD/mR1. Packaging of retroviral vector and preparation of viral stock were accomplished by using ψ2 and PA317 cell lines, as we have described previously [Fan, et al., 1996a; 1996b], except that PA317-derived stable packaging lines were obtained by selection with histidinol for 15 days. To obtain an expression vector for R1 in the antisense orientation, mouse R1 cDNA was prepared by PCR using the primers GCCTCGAGCT-GACAGTCGTCTCTGTCCCT (SEQ ID No:4) and TAAAGCTTATCACTTAGAAATGTTTATTTCAAAAT (SEQ ID No:5), digested with XhoI and HindIII, and inserted into the mammalian expression plasmid pcDNA3 (Invitrogen Corp.), to give the plasmid pASR1. The construction of both pSHD/mR1 and pASR1 was confirmed by sequencing analysis as well as restriction by endonuclease digestions. Cell Lines and Cell Culture. Cell lines used in this study and related information are shown in Table 1. Cells were routinely cultured in a-minimal essential medium (MEM) supplemented with 8% calf serum (Fetalclone III, Hyclone). To generate cells expressing recombinant R1, cells were infected with SHD/mR1 viral stock, prepared from the stable packaging line PA/mR1, in the presence of polybrene [Fan, et al., 1996a; Miller, et al., 1993]. Stable infectants (≧500 clones) were obtained by selection with 4–15 mM histidinol depending on the cell lines, and were pooled and expanded. Control cell lines were generated in parallel by using LXSHD virus lacking the R1 sequence. R1 antisense expressing cells were generated by transfection of NIH 3T3 cells using a LipofectAmine kit (Life Technologies) followed by selection with G418 [Egan, et al., 1987a; Taylor, et al., 1992]. Cell growth rates were assessed by measuring absorbance at 260 nm in cell extracts prepared in 1.0 N NaOH [Kempe, et al., 1976], and/or by counting cells at different time points after seeding [Egan, et al., 1987a]. Growth in soft agar was estimated in 10 cm tissue culture plates containing 15 ml of base agar (0.5% Bacto agar in MEM containing 10% calf serum), and 10 ml of growth agar (0.33% agar in MEM containing 10% calf serum). Cells were obtained from subconfluent cultures and colonies were scored 14–21 days later [Fan, et al., 1996a; 1996b; Taylor, et al., 1992].

Assays for Tumorigenicity and Metastasis. C3H/HeN syngeneic mice (Charles River Breeding Laboratories, Quebec) were used in these assays as previously described [Fan, et al., 1996a; Egan, et al., 1987b]. Cells were prepared from subconfluent, logarithmically growing cultures, collected by gentle treatment with trypsin/EDTA solution and adjusted to appropriate concentration. Tumor latency was determined by injecting cells subcutaneously and recording the time required to form a tumor (2×2 mm) detectable by palpation. Tumors were removed from the mice and tumor weight was recorded 21 days later. In the case of no tumor formation, mice were kept for 2 months after injection and then sacrificed. For metastasis assays, cells were injected into the tail veins of 6–8 week old C3H/HeN syngeneic mice and an estimate of the number of lung tumors was made 21 days later, as described [Fan, et al., 1996a; Egan, et al., 1987b]. To confirm that equal numbers of test and control cells were injected, duplicate culture plates containing growth medium were inoculated with 100 cells per plate. After 10 days in culture, plates were stained with methylene blue and colonies were scored.

Detection of Recombinant R1 Protein Expression. An indirect immunofluorescence assay was used to detect transient expression of recombinant R1 protein in BHK cells [Fan et al, 1996a,b]. Seventy percent confluent cells growing on coverslips were transfected with pSHD/mR1 plasmid using a LipofectAmine reagent. At 20 hours after transfection, cells were fixed with 3% formaldehyde prepared in phosphate buffered saline, pH 7.2 (PBS), permeabilized with 0.1% Triton X-100 (in PBS), incubated with anti-Myc epitope monoclonal 9E10 antibody (American Type Culture Collection), washed, reacted with goat anti-mouse IgG (full molecule) FITC conjugate (Sigma), washed again and finally examined under a fluorescence microscope [Leonhardt, et al.]. Immunoprecipitation of recombinant R1, by the 9E10 antibody, from [$^{35}$S] methionine/cystein-labelled cells was performed using previously described procedures [McClarty, et al, 1990; Goding, 1978]. In some experiments R1 protein levels were determined by Western blot analysis using anti-R1 monoclonal antibody, AD203, as described previously [McClarty, et al, 1990; Fan, et al., 1996a].

Ribonucleotide Reductase Assay. Ribonucleotide reductase activity in crude extracts prepared from SC2/mR1 and control SC2/SHD cell lines was assayed as previously described [Lewis, 1978; Hurta and Wright, 1992; Hurta, et al., 1991]. In some experiments, enzyme assays were performed by combining purified recombinant R2 protein with 9E10 antibody-precipitated R1 protein. Pansorbin cells (formaldehyde fixed Staphylococci, Calbiochem, La Jolla, Calif.) carrying surface protein A and rabbit anti-mouse IgG was prepared as described [Goding, 1978]. This conjugate was further incubated with an excess amount of 9E10 antibody and washed five times. Twenty μl of this complex (10% suspension) was added into 1.0 ml of extract prepared from 5×10$^7$ cells and placed on a rocker at 4° C. for 2 hours, washed three times with PBS containing 10 mg/ml bovine serum albumin, and assayed for ribonucleotide reductase activity after the addition of 1.0 μg of purified recombinant R2 protein [Hurta and Wright, 1992; Fan, et al., 1996a; Mann, et al., 1991]

EXAMPLE 1

Figure 1B:
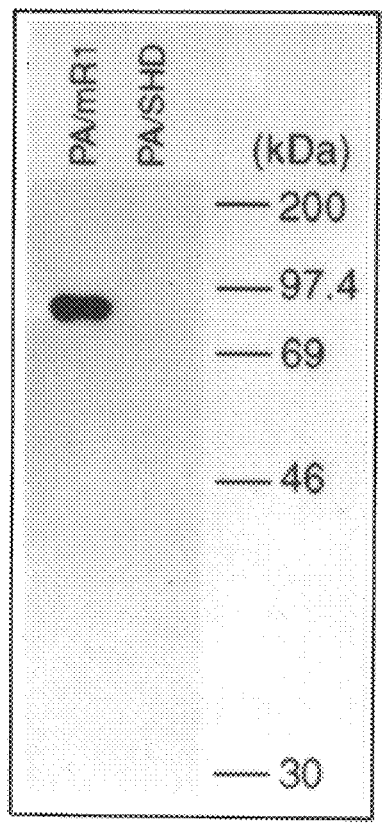

Expression of Recombinant R1. To overexpress the R1 protein in cells, a mammalian expression vector pSHD/mR1 was constructed. In this vector, the expression of the human Myc-epitope tagged R1 cDNA is under the control of a retroviral promoter, long terminal repeat sequence [Miller, et al., 1993]. The expression of recombinant R1 was first analyzed in BHK cells following transient transfection. An indirect immunofluorescence assay using the anti-Myc monoclonal 9E10 antibody revealed cytoplasmic expression of the recombinant R1 protein in pSHD/mR1 transfected cells (FIG. 1A). As a control, non-transfected or empty vector pLXSHD transfected cells did not show any specific fluorescence. After demonstrating that the recombinant R1 protein can be expressed in mammalian cells, we then converted the expressible DNA into an infectious, but replication-deficient vector virus which has a high delivery efficiency, by using retroviral packaging cells. The expression of recombinant R1 in the stable packaging line PA/mR1 was again analyzed. Immunoprecipitation using the 9E10 antibody detected a single approximately 88 kDa protein from extract prepared from PA/mR1 cells (Table 1), which had been metabolically labelled with [$^{35}$S] methionine/cystein (FIG. 1B). As expected, no protein was precipitated from the stable control virus packaging cell line PA/SHD (FIG. 1B). These results indicated that stable expression of the recombinant R1 protein could be achieved.

It was then determined if cell-expressed recombinant R1 is biologically active. For this study a hydroxyurea resistant mouse L cell line, SC2, was infected with SHD/mR1 or LXSHD viral vectors and was used to select stable infectants (Table 1). Since SC2 cells express more R2 relative to the R1 subunit, expression of biologically active R1 protein in this cell line would result in increased ribonucleotide reductase activity [McClarty, et al, 1990]. In four experiments, the CDP reductase activity in the crude extract prepared from SC2/mR1 cells was 13.2±0.7 nmoles/mg protein/hr, which is approximately 30% higher than that in extract prepared from control SC2/SHD cells (10.1±0.2 nmoles/mg/hr). Furthermore, the recombinant R1 from C1/mR1 cells was immunoprecipitated using the 9E10 antibody, and was used to assay ribonucleotide reductase activity by combining the washed immunoprecipitate with purified recombinant R2 protein [Hurta and Wright, 1992; Fan, et al., 1996a; Mann, et al., 1991]. In three independent experiments, enzyme activity of 15.4±2.0 pmoles/mg/hr was detected when C1/mR1 cells (Table 1) were used as a source of recombinant R1, and as expected no activity was found when control C1/SHD (Table 1) cells were used.

EXAMPLE 2

Figure 2:
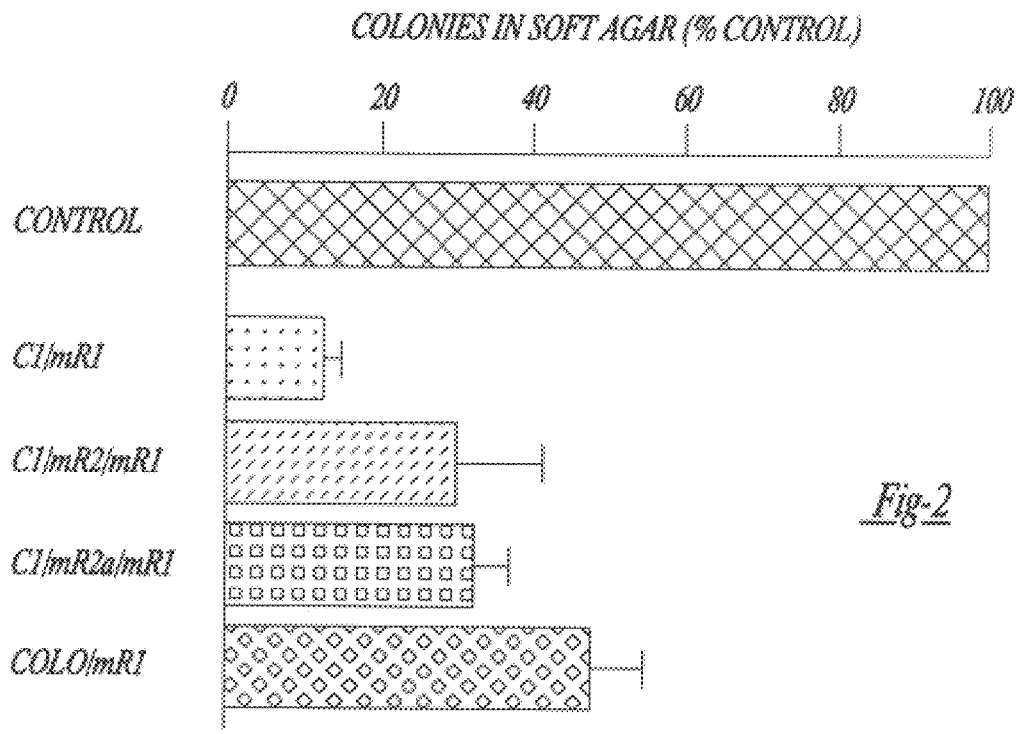
FIG. 2 is a bar graph showing reduced growth efficiency in soft agar with recombinant R1 expressing cells. Cell lines stably infected with the R1 viral vector were compared to appropriate empty vector-infected control cell lines (Table 1). Data presented were obtained from at least three independent experiments each consisting of triplicate plates per cell line. Inoculum sizes (cells/plate) were as followings: $5\times10^5$ for C1/SHD and C1/mR1 cells, $1\times10^5$ for C1/mR2 and C1/mR2/mR1 cells, $1\times10^4$ for C1/mR2a/SHD and C1/mR2a/mR1 cells, ras-3/SHD and ras-3/mR1 cells, and $1\times10^3$ for Colo/SHD and Colo/mR1 cells. In all the cases, the difference, in numbers of colonies formed, between recombinant R1 expressing cells and the control cells were statistically significant ($p<0.001$).

Reduced Anchorage Independence by Cells that Overexpress R1. Cellular transformation is frequently accompanied by anchorage independent growth in vitro, which often correlates with tumorigenic potential in vivo, and can be evaluated by the ability to proliferate and form colonies in medium containing agar [Fan, et al., 1996a; Egan, et al., 1987a]. To investigate the role that R1 may play in cellular transformation CIRAS-1 cells were infected with the PA/mR1 viral vector or the empty virus control LXSHD (Table 1). CIRAS-1 cells were derived from wild type, non-malignant mouse 10T½ cells by transfection with oncogenic T24 H-ras [Egan, et al., 1987a]. Previous studies have shown that it is a moderately malignant cell line, and can serve as a good model for analyzing transformation and malignancy related characteristics [Hurta and Wright, 1995; Fan, et al., 1996a; Egan, et al., 1987a; Wright, et al., 1993]. Stable infectants obtained after histidinol selection were evaluated for soft agar growth abilities. It was found that the efficiency in forming colonies in soft agar by C1/mR1 cells that contained elevated levels of R1, was significantly decreased as compared to control C1/SHD cells (FIG. 2). The effects of R1 expression was also tested on soft agar growth with cells containing deregulated R2 expression. C1/mR2 is a CIRAS-1 derivative expressing recombinant R2, and has acquired an increased malignant potential [Fan, et al., 1996a]. Again it was observed that colony forming efficiency of C1/mR2/mR1 cells with elevated R1 was significantly reduced, when compared to control C1/mR2 cells (FIG. 2).

To exclude the possibility (albeit unlikely) that the reduced soft agar growth efficiencies observed with R1 cells may have resulted from selection of cells with intrinsically lower growth efficiencies from a relatively heterogeneous cell population, a subclone designated C1/mR2a was isolated from C1/mR2 cells. Two cell lines (C1/mR2a/mR1 and control C1mR2a/SHD) were derived from this subclone population (Table 1). Consistent with the observations with the parental line, C1/mR2a/mR1 cells exhibited similar reductions in growth efficiencies in soft agar, when compared to control C1/mR2a/SHD cells (FIG. 2). This shows that the reduced anchorage-independence is brought about by recombinant R1 expression.

EXAMPLE 3

The above tested cell lines are of mouse origin. To determine whether or not expression of recombinant R1 in human tumor cells also alters transformation characteristics as demonstrated by changes in soft agar growth ability, the human colon adenocarcinoma Colo 320HSR cell line [Quinn, et al., 1979] was used. These cells were infected with the viral vector containing the R1 sequence to obtain the Colo/mR1 cell line (Table 1). Interestingly, growth efficiency in soft agar with Colo/mR1 cells was decreased by about 50% when compared to Colo/SHD cells containing the empty vector (FIG. 2).

EXAMPLE 4

Suppression of Tumorigenic and/or Metastatic Potential in vivo with Cells Containing Elevated R1. To further evaluate the role that alterations in R1 expression may play in malignant progression, tumorigenic and metastatic properties of C1/mR1 cells were analyzed in in vivo models. C1/mR1 cells exhibited a dramatic reduction in malignant potential when compared to control C1/SHD cells (Table 2). Whereas all mice injected subcutaneously with C1/SHD cells developed tumors at about 11 days after injection, none of the animals injected with C1/mR1 cells formed detectable tumors even up to two months after injection. In addition, experimental metastasis assays showed that C1/mR1 cells were much less efficient at forming lung metastases as compared to the control C1/SHD cells (Table 2). Similar experiments were performed with another independently selected T24 H-ras transfected mouse 10T1/2 cell line called ras-3, which has been described previously [Taylor, et al., 1992]. Although the tumor suppressing activity of the recombinant R1 in ras-3 cells was not as great as was observed in C1RAS-1 derived cells, tumorigenicity with ras-3/mR1 cells, as compared to control ras-3/SHD cells, was significantly reduced as judged by an extended tumor latency and smaller tumor sizes. Similar to the CIRAS-1 derived cells, ras-3/mR1 cells exhibited a markedly reduced metastatic potential when compared to the control ras-3/SHD cells (Table 2).

Also tested in vivo was the impact of recombinant R1 expression on malignant potential with cells that contained deregulated R2 expression. Consistent with previous observations, C1/mR2 cells showed higher tumorigenic and metastatic potential than control C1/SHD cells, confirming the malignancy promoting function of R2 [Fan, et al., 1996a]. Also in agreement with the data obtained in in vitro experiments (FIG. 2), C1/mR2/mR1 cells, were much less malignant than control C1/mR2 cells (Table 2). Further, both the tumorigenic and the metastatic potential of C1/mR2/mR1 cells were reduced to significantly lower levels than that of C1/SHD cells (Table 2).

The potential ability of recombinant R1 expression to modify the malignant properties of a highly malignant cell line that contains multiple oncogene alterations was then tested. The RMP-6 mouse 10T1/2 line, which has been transfected with a combination of activated H-ras, c-myc and a mutated oncogenic form of p53, has been well characterized [Taylor, et al., 1992; Huang, et al., 1995], and was used in these studies. Unlike the above R1 overexpressing cell lines studied, RMP/mR1 cells (Table 1) did not show changes in tumorigenicity when compared to control RMP/SHD cells (Table 2). In agreement with these in vivo results, it was observed that RMP/mR1 and RMP/SHD cells had approximately the same colony forming efficiencies in soft agar growth experiments. Interestingly, however, RMP/mR1 cells formed significantly fewer lung tumors in syngeneic mice than control RMP/SHD cells in experimental metastasis assays (Table 2). The difference in numbers of lung metastases shown in Table 2 may actually have been underestimated, since lung tumors were generally larger in mice that had received RMP/SHD cells than those that developed in the lungs of mice injected with RMP/mR1 cells. These results indicate that overexpression of R1 in highly malignant RMP-6 cells markedly suppresses metastatic potential.

EXAMPLE 5

Figure 3A:
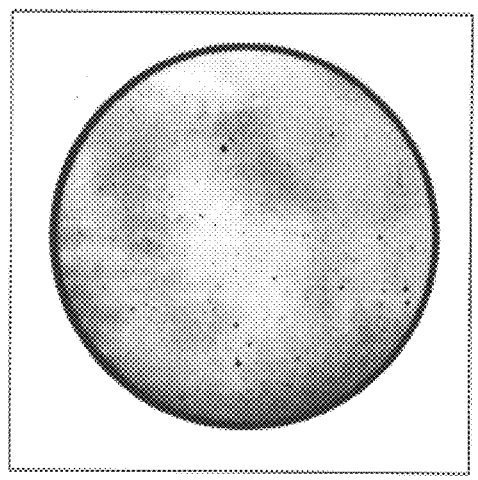
FIG. 3 are photographs of plates showing increased colony forming efficiency in soft agar with N/ras&ASR1 cells (B) as compared to control N/ras cells (A). Each plate was inoculated with $1\times10^4$ cells. N/ras&ASR1 cells formed at least four times more colonies, which were generally larger than those formed by N/ras cells. The colonies shown in (A) developed after 3 weeks and those shown in (B) developed after 2 weeks of incubation. When data from six experiments each consisting of four plates per cell line were analyzed, the difference in colony forming efficiencies exhibited by the two cell lines were found to be highly significant ($p<0.0001$)
Figure 3B:
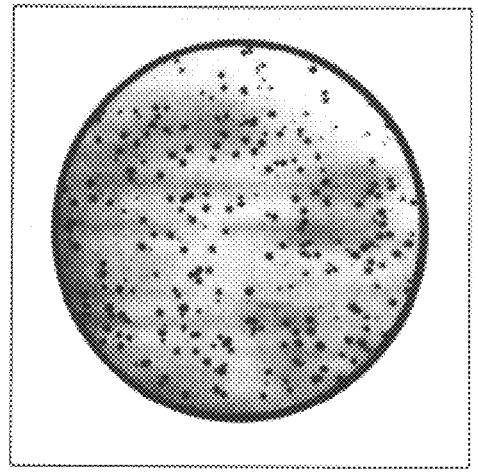
Figure 4A:
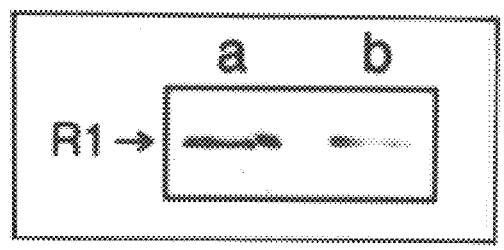
FIG. 4A–B are photographs showing the results of (A) Western blot analysis showing reduced R1 protein in N/ras&ASR1 (b) as compared to control N/ras cells (a) and (B) India ink staining of the nitrocellulose membrane [Wright and Anazodo, 1996], shown in (A), demonstrating approximately equal loading of cell extracts.
Figure 4B:
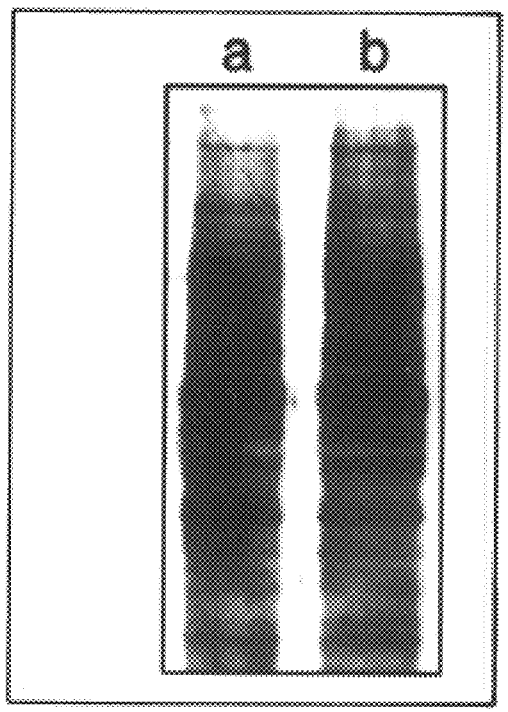

Increased Anchorage Independence with Oncogenic ras-transfected Cells Expressing R1 in the Antisense Orientation. Expression of an antisense sequence is a commonly used approach to achieve down regulated gene expression [Spearman, et al., 1994; Wright and Anazodo, 1996]. If R1 can inhibit cellular transformation as indicated above, expression of an R1 antisense sequence should reduce the levels of the R1 protein, and further increase transformation characteristics. To test this, an expression vector was constructed, in which the R1 sequence has been placed in an antisense orientation relative to the vector promoter. NIH 3T3 cells were co-transfected with the antisense vector and the pH06Ti plasmid that expresses the T24 H-ras oncogene [Egan, et al., 1987a]. H-ras expression transforms mammalian cells so that they are often capable of colony formation in soft agar containing growth medium [Fan, et al., 1996a; Egan, et al., 1987a]. Stable co-transfectants obtained after selection with G418 were evaluated for anchorage independent growth. In agreement with the results obtained in experiments described above, N/ras&ASR1 cells containing R1 antisense exhibited a dramatically higher colony forming efficiency in soft agar, when compared to control N3/ras cells that contained the H-ras oncogene without the R1 antisense sequence (FIG. 3). Western blot analysis (FIG. 4), and Northern blot analysis indicated, as expected, lower expression of R1 in N/ras&ASR1 cells than in N/ras cells. The growth rates of N/ras&ASR1 and N/ras cells on the surface of plastic culture plates were approximately the same, with doubling times of 14 to 16 hours.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Information about cell lines

| Designate | Parental line | Related characteristics and transgene expression | Reference or source |
|---|---|---|---|
| BHK | | | ATCC |
| ψ2 | | Retroviral packaging | ATCC |
| PA317 | | Retroviral packaging | ATCC |
| PA/SHD | PA317 | Packaging control virus LXSHD | This study |
| PA/mR1 | PA317 | Packaging SHD/mR1* virus | This study |
| SC2 | L60 | R2 is in excess as compared to R1 | McClarty et al. |
| SC2/SHD | SC2 | hisD† | This study |
| SC2/mR1 | SC2 | mR1, hisD† | This study |
| CIRAS-1 | 10T½ | T24 H-ras | Egan et al. |
| C1/SHD | CIRAS-1 | hisD†, T24 H-ras | This study |
| C1/mR1 | CIRAS-1 | mR1*, hisD†, T24 H-ras | This study |
| C1/mR2 | CIRAS-1 | mR2*, T24 H-ras | Fan et al. |
| C1/mR2/SHD | C1/mR2 | hisD†, mR2*, T24 H-ras | This study |
| CI/mR2/mR1 | C1/mR2 | mR1, hisD†, mR2*, T24 H-ras | This study |
| C1/mR2a/SHD | C1/mR2a‡ | hisD†, mR2*, T24 H-ras | This study |
| C1/mR2a/mR1 | C1/mR2a‡ | mR1*, hisD†, mR2*, T24 H-ras | This study |
| ras-3 (or R-3) | 10T½ | T24 H-ras, | Taylor et al. |
| ras-3/SHD | ras-3 | hisD†, T24 H-ras | This study |
| ras-3/mR1 | ras-3 | mR1†, hisD†, T24 H-ras | This study |
| RMP-6 | 10T½ | T24 H-ras, c-myc, mutant p53 | Taylor et al. |
| RMP/SHD | RMP-6 | hisD†, T24 H-ras, c-myc, mutant p53 | This study |
| RMP/mR1 | RMP-6 | mR1*, hisD†, T24 H-ras, c-myc, mutant p53 | This study |
| Colo 320HSR | | Human colon carcinoma | ATCC |
| Colo/SHD | Colo 320HSR | hisD† | This study |
| Colo/mR1 | Colo 320HSR | mR1*, hisD† | This study |
| NIH 3T3 | | | ATCC |
| N/ras | NIH3T3 | T24 H-ras, neo† | This study |
| N/ras & ASR1 | NIH3T3 | R1 antisense, T24 H-ras, neo† | This study |

ATCC, American Type Culture Collection.
*mR1 and mR2, human Myc epitoped-tagged R1 and R2 proteins, respectively.
†Selective marker genes, hisD (histidinol dehydrogenase), and neo (neomycin phosphotransferase).
‡C1/mR2a is a subclone derived from C1/mR2.

TABLE 2

Decreased tumorigenic and metastatic potential with cells expressing recombinant R1 protein

| | Tumorigenicity assay* (subcutaneous tumors) | | | Metastasis assay† (lung tumors) | | |
|---|---|---|---|---|---|---|
| Cell line | Frequency | Latency (days) | Weight (g) | Frequency | Number of tumors | P |
| C1/SHD | 5/5 | 11 ± 2 | 0.3 ± 0.1 | 5/5 | 44 ± 13 | |
| C1/mR1 | 0/5 | — | — | 5/5 | 6 ± 3 | <0.001 |
| ras-3/SHD | 5/5 | 9 ± 2 | 0.9 ± 0.3 | 5/5 | 120 ± 22 | |
| ras-3/mR1 | 4/5 | 14 ± 2 | 0.3 ± 0.2 | 4/5 | 4 ± 2 | <0.001 |
| C1/mR2 | 10/10 | 8 ± 1 | >1.0‡ | 10/10 | 195 ± 34 | |
| C1/mR2/mR1 | 2/10‡ | 19 ± 4 | <0.1‡ | 10/10 | 20 ± 6 | <0.001 |
| RMP/SHD | 4/4 | 7 ± 1 | 1.1 ± 0.3 | 4/4 | 61 ± 8 | |
| RMP/mR1 | 4/4 | 7 ± 1 | 1.0 ± 0.2 | 4/4 | 27 ± 7 | <0.001 |

*Number of cells injected subcutaneously were as the follows: 1 × 10⁵ for RMP/SHD and RMP/mR1 cells, and 3 × 10⁵ for all other cell lines.
†Number of cells injected intravenously were: 2 × 10⁵ for RMP/SHD and RMP/mR1 cells, and 1 × 10⁶ for all other cell lines.
‡Mice injected with C1/mR2 cells were sacrificed 21 days after injection. Tumors from these mice were estimated to be at least 1.0 g. One of the mice injected with C1/mR2/mR1 developed tumor on day 15; when this mouse was killed on day 21, the tumor was estimated to be less than 0.1 g. Another mouse in this group had an extremely slow-growing tumor, which became detectable on day 23 and was estimated to be less than 0.1 g on day 60.

References

Amara et al., 1994. Phorbol ester modulation of a novel cytoplasmic protein binding activity at the 3'-untranslated region of mammalian ribonucleotide reductase R2 mRNA and role in message stability. J. Biol. Chem. 269:6709–7071.

Amara et al., 1995A. Altered regulation of message stability and tumor promoter-responsive cis-trans interactions of ribonucleotide reductase R1 and R2 messenger RNAs in hydroxyurea-resistant cells. Cancer Res. 55:4503–4506.

Amara et al., 1995B. Defining a novel cis element in the 3'-untranslated region of mammalian ribonucleotide reductase component R2 mRNA: Role in transforming growth factor-$\beta_1$ induced mRNA stabilization. Nucleic Acids Res. 23:1461–1467.

Amara et al. 1996. Defining a novel cis-element in the 3'-untranslated region of mammalian ribonucleotide reductase component R2 mRNA: cis-trans interactions and message stability. J. Biol. Chem. 271:20126–20131.

Ashihara and Baserga, 1979. Cell Synchronization. Methods Enzymol. 58:248–262.

Betz et al., 1994, Basic Neurochem. Molecular Cell, (Raven Press Ltd, New York) 5th Ed., 681–699

Bickel, et al., 1993, "Pharmacologic effects in vivo in brain by vector-mediated peptide drug delivery" Proc. Natl. Acad. Sci. USA 90(7)2618–2622

Blaesse, 1997. Gene Therapy for Cancer. Scientific American 276(6):111–115.

Björklund, et al., 1990. Biochemistry, 29:5452–5458

Björklund et al., 1993. Structure and promoter characterization of the gene encoding the large subunit (R1 Protein) of mouse ribonucleotide reductase. Proc. Natl. Acad. Sci. USA 90:11322–11326.

Brem et al., "Polymers as controlled drug delivery devised for the treatment of malignant brain tumors" Eur. J. Pharm. Biopharm 39:2–7 (1993)

Capecchi, "Altering the genome by homologous recombination" Science 244:1288–1292 (1989).

Caras, et al 1985. Cloned Mouse Ribonucleotide Reductase Subunit M1 cDNA Reveals Amino Acid Sequence Homology with *Escherichia coli* and Herpesvirus Ribonucleotide Reductases. Biol Chem. 260:7015–7022.

Chan et al., 1993. Phosphorylation of ribonucleotide reductase R2 protein: in vivo and in vitro evidence of a role for p34$^{cdc2}$ and CDK2 protein kinases. Biochemistry 32:12835–12840.

Chen et al., 1993. Mammalian ribonucleotide reductase R1 mRNA stability under normal and phorbol ester stimulating conditions: involvement of a cis-trans interaction at the 3'-untranslated region. EMBO J., 12:3977–3986.

Chen et al., 1994A. Regulation of mammalian ribonucleotide reductase R1 mRNA stability is mediated by a ribonucleotide reductase R1 mRNA 3'-untranslated region cis-trans interaction through a protein kinase C-controlled pathway. Biochem. J. 302:125–132.

Chen et al., 1994B. Defining a novel ribonucleotide reductase R1 mRNA cis element that binds to an unique cytoplasmic trans-acting protein. Nucleic Acids Res., 22:4796–4797.

Choy et al., 1988. Molecular mechanisms of drug resistance involving ribonucleotide reductase: hydroxyurea resistance in a series of clonally related mouse cell lines selected in the presence of increasing drug concentrations. Cancer Res. 48:2029–2035.

Culver, 1998. Site-Directed recombination for repair of mutations in the human ADA gene. (Abstract) Antisense DNA & RNA based therapeutics, February, 1998, Coronado, Calif.

Davis et al., 1994. Purification, Characterization, and Localization of Subunit Interaction Area of Recombinant Mouse Ribonucleotide Reductase R1 Subunit. Biol. Chem. 269:23171–23176.

Egan, et al., 1987A. Expression of H-ras Correlates with Metastatic Potential: Evidence for Direct Regulation of the Metastatic Phenotype in 10T1/2 and NIH 3T3 Cells. Mol. Cell. Biol. 7:830–837.

Egan et al., 1987B. Transformation by oncogenes encoding protein kinases induces the metastatic phenotype. Science 238:202–205.

Eriksson et al., 1984. Cell cycle-dependent regulation of mammalian ribonucleotide reductase. The S phase-correlated increase in subunit M2 is regulated by de novo protein synthesis. J. Biol. Chem. 259:11695–11700.

Fan et al., 1996A. Ribonucleotide reductase R2 component is a novel malignancy determinant that cooperates with activated oncogenes to determine transformation and malignant potential. Proc. Natl. Acad. Sci. USA 93:14036–14040.

Fan et al., 1996B. A link between ferritin gene expression and ribonucleotide reductase R2 protein, as demonstrated by retroviral vector mediated stable expression of R2 cDNA. FEBS Lett. 382:145–148.

Fan et al., 1996C. Cloning of a gene from Chlamydia trachomatis that complements thymidylate synthase-deficient *Escherichia coli*. In: Abstracts of the 94th General Meeting of the American Society for Microbiology, p. 134.

Filatov et al., 1996. Induction of the mouse ribonucleotide reductase R1 and R2 genes in response to DNA damage by UV light. J. Biol. Chem. 271:23698–23704.

Gilboa et al., 1986. Transfer and expression of cloned genes using retroviral vectors. BioTechniques 4(6):504–512.

Gingras, et al., 1991. Cancer Res. 50:4061–4066.

Glenney, 1986. Anal. Biochem. 79:4002–4005.

Goding, 1978. J. Immunol. Methods 20:241–253.

Hanania, et al 1995. Recent advances in the application of gene therapy to human disease. Am. J. Med. 99:537.

Huang et al., 1995. Multiple effects on drug sensitivity, genome stability and malignant potential by combinations of H-as, c-myc and mutant p53 gene overexpression. Int. J. Oncol. 7:57–63.

Hurta, et al., 1991. Early induction of ribonucleotide reductase gene expression by transforming growth factor $\beta_1$ in malignant H-ras transformed cell lines. J. Biol. Chem. 266:24097–24100.

Hurta and Wright, 1992 J. Biol. Chem. 267:7066–7071

Hurta and Wright, 1994. Alterations in the cyclic AMP signal transduction pathway regulating ribonucleotide reductase gene expression in malignant H-ras transformed cell lines. J. Cell. Physiology 158:187–197.

Hurta and Wright, 1995. Malignant transformation by H-ras results in aberrant regulation of ribonucleotide reductase gene expression by transforming growth factor-$\beta_1$. J. Cell. Biochem. 57:543–556.

Jensen et al., 1994. Identification of genes expressed in premalignant breast disease by microscopy-directed cloning. Proc. Natl. Acad. Sci, USA. 91:9257–9261.

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203:88–99.

Kempe, et al., 1976. Cell 9:541–550.

Kozak, 1987. Nucleic Acids Res. 20:8125–8148.

Lewis et al., 1978. Assay of ribonucleotide reduction in nucleotide-permeable hamster cells. J. Cell Physiol. 94:287–298.

Leonhardt, et al., Cell 71: 865–873.

Mader, et al., 1996. Proceedings of the Eighty-seventh Annual Meeting, American Association of Cancer Research 37:547.

Mann et al., 1988. Ribonucleotide reductase M1 subunit in cellular proliferation, quiescence, and differentiation. J. Cancer Res. 48:5151–5156.

Mann, et al., 1991. Biochemistry 30:1939–1947.

McClarty et al., 1990. Increased ferritin gene expression is associated with increased ribonucleotide reductase gene expression and the establishment of hydroxyurea resistance in mammalian cells. J. Biol. Chem. 265:7539–7547.

Miller et al., 1993. Use of retroviral vectors for gene transfer and expression. Meth. Enzymol. 217:581–599.

Pardridge, et al., 1992, "Blood-brain barrier and new approaches to brain drug delivery" West J. Med. 156(3) 281–286

Pardridge, 1992, "Recent Developments in peptide drug delivery to the brain" Pharm. Toxicol. 71(1):3–10

Quinn, et al., 1979. Cancer Res. 39:4914–4924.

Reichard, 1993. From RNA to DNA, why so many ribonucleotide reductases? Science 60:1773–1777.

Saeki et al., 1995. Immunohistochemical detection of ribonucleotide reductase in human breast tumors. Int. J. Oncol. 6:523–529.

Spearman et al., 1994. Antisense oligodeoxyribonucleotide inhibition of TGF-$\beta_1$ gene expression and alterations in the growth and malignant properties of mouse fibrosarcoma cells. Gene 149:25–29.

Stubbe, 1989. Protein radical involvement in biological catalysis? Annu. Rev. Biochem. 58:257–285.

Taylor et al., 1992. Evidence for synergistic interactions between ras, myc and a mutant form of p53 in cellular transformation and tumor dissemination. Oncogene 7:1383–1390.

Thelander et al., 1985. Subunit M2 of mammalian ribonucleotide reductase. Characterization of a homogeneous protein isolated from M2-overproducing mouse cells. J. Biol. Chem. 260:2737–2741.

Thelander et al., 1980. Ribonucleotide reductase from calf thymus. Separation of the enzyme into two nonidentical subunits, proteins M1 and M2. J. Biol. Chem. 255:7426–7432.

Thelander and Berg, 1986. Mol. Cell. Biol. 6:3433–3442.

Thelander, et al 1990. J. Biol. Chem. 255:7624–7432

Tonin et al., 1987. Chromosomal assignment of amplified genes in hydroxyurea resistant hamster cells. Cytogenet. Cell Genet. 45:102–108.

Weber, 1983. Biochemical strategy of cancer cells and the design of chemotherapy. Cancer Res. 43:3466–3492.

Wright & Anazodo, 1996. Antisense Molecules and Their Potential For The Treatment Of Cancer and AIDS. Cancer J. 8:185–189.

Wright, 1989A. Altered mammalian ribonucleotide reductase from mutant cell lines. Encycl. Pharmacol. Therapeut. 128:89–111.

Wright, et al., 1989B *Hydroxyurea and related compounds in Drug Resistance in Mammalian Cells*. R. S. Gupta Ed. (CRC Press, Boca Raton, Fla., 1989), Vol. 1, pp 15–27.

Wright et al., 1990A. Regulation and drug resistance mechanisms of mammalian ribonucleotide reductase and the significance to DNA synthesis. Biochem. Cell Biol. 68:1364–1371.

Wright,et al., 1990b Anticancer Res. 10:1247–1256.

Wright et al., 1993. Transforming growth factor β and fibroblast growth factor as promoters of tumor progression to malignancy. Crit. Rev. Oncogen. 4:473–492.

---

What is claimed is:

1. A method for inhibiting growth of a neoplastic cell in a mammal, the method comprising the step of increasing the expression of ribonucleotide reductase R1 by administering directly into said neoplastic cell a nucleic acid molecule encoding a ribonucleotide reductase R1, whereby the expression of said ribonucleotide reductase R1 is increased and inhibits the growth of said neoplastic cell.

2. The method of claim 1, wherein the nucleic acid molecule is SEQ ID NO: 1.

3. The method of claim 1 or 2, wherein the nucleic acid molecule is in the form of a vector.

4. The method of claim 3, wherein the vector is a retroviral vector.

5. The method of claim 1, wherein said mammal is a human.

6. A method for inhibiting the malignant growth of a neoplastic cell in a mammal, the method comprising the step of increasing the expression of ribonucleotide reductase R1 by administering directly into said neoplastic cell a nucleic acid molecule encoding a ribonucleotide reductase R1, whereby the expression of said ribonucleotide reductase R1 is increased and inhibits the malignant growth of said neoplastic cell.

7. The method of claim 6, wherein the nucleic acid molecule is SEQ ID NO: 1.

8. The method of claim 6 or 7, wherein the nucleic acid is in the form of a vector.

9. The method of claim 8, wherein the vector is a retroviral vector.

10. The method of claim 6, wherein said mammal is a human.

* * * * *

UNITED STATES PATENT AND TRADEMARK OFFICE
CERTIFICATE OF CORRECTION

PATENT NO. : 6,472,376 B2
DATED : October 29, 2002
INVENTOR(S) : Wright et al.

It is certified that error appears in the above-identified patent and that said Letters Patent is hereby corrected as shown below:

<u>Title page,</u>
Item [73], Assignee, remove the comma after "Technologies" and before "Inc." so that the assignee appears as:

-- [73] Assignee: Genesense Technologies Inc., Toronto, (CA) --

Signed and Sealed this

Fifteenth Day of April, 2003

JAMES E. ROGAN
*Director of the United States Patent and Trademark Office*